United States Patent [19]

Maltby et al.

[11] Patent Number: 4,757,252

[45] Date of Patent: Jul. 12, 1988

[54] PROBE SYSTEM FOR MEASURING THE CONDITION OF MATERIALS

[75] Inventors: Frederick L. Maltby, Jenkintown; Edward R. Woerner, North Wales; Thomas E. Meacham, Jr., Holland; Steven R. Petersen, Ambler, all of Pa.

[73] Assignee: Drexelbrook Controls, Inc., Horsham, Pa.

[21] Appl. No.: 791,303

[22] Filed: Oct. 25, 1985

[51] Int. Cl.⁴ .................. G01N 27/22; G01F 23/26; G01G 11/04
[52] U.S. Cl. .................. 324/61 P; 340/620; 73/304 C; 361/284
[58] Field of Search .............. 361/284; 73/304 C; 324/61 P, 61 R; 340/620

[56] References Cited

U.S. PATENT DOCUMENTS

| | | | |
|---|---|---|---|
| 2,752,543 | 6/1956 | Smith | 361/284 |
| 2,904,751 | 9/1959 | Parsons | 361/284 |
| 2,950,426 | 8/1960 | Frome | 361/284 |
| 2,998,559 | 8/1961 | Smith | 361/284 |
| 3,079,797 | 3/1963 | Hermanson . | |
| 3,109,882 | 11/1963 | Maltby | 361/284 |
| 3,262,032 | 7/1966 | Levine | 361/284 |
| 3,285,068 | 11/1966 | Morris . | |
| 3,748,551 | 7/1973 | Petersen | 361/284 |
| 3,781,672 | 12/1973 | Maltby | 73/304 C |
| 3,843,832 | 10/1974 | Petersen | 361/284 |
| 3,918,306 | 11/1975 | Maltby . | |
| 4,064,753 | 12/1977 | Sun et al. . | |
| 4,165,641 | 8/1979 | Pomerantz | 361/284 |
| 4,166,388 | 9/1979 | Sun et al. . | |
| 4,184,369 | 1/1980 | Jung | 361/284 |
| 4,208,909 | 6/1980 | Maltby et al. . | |
| 4,428,026 | 1/1984 | Maltby | 73/304 C |
| 4,530,372 | 7/1985 | Overton | 73/304 C |
| 4,574,328 | 3/1986 | Maier | 361/284 |

Primary Examiner—Reinhard J. Eisenzopf
Assistant Examiner—Jose M. Solis
Attorney, Agent, or Firm—Woodcock Washburn Kurtz Mackiewicz & Norris

[57] ABSTRACT

A probe comprises a plurality of longitudinally extended conductors forming a probe electrode, a laterally displaced ground electrode and two laterally displaced active guard electrodes interposed between the probe electrode and the ground electrode. The conductors are surrounded by solid insulation and the probe guard electrodes are driven at substantially the same potential as the probe electrode. The probe is utilized to measure the condition of materials in which the probe is immersed.

22 Claims, 4 Drawing Sheets

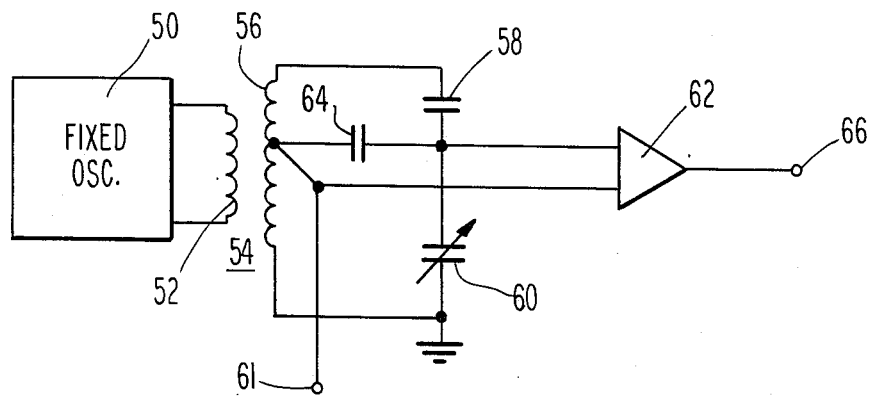
Fig. 6
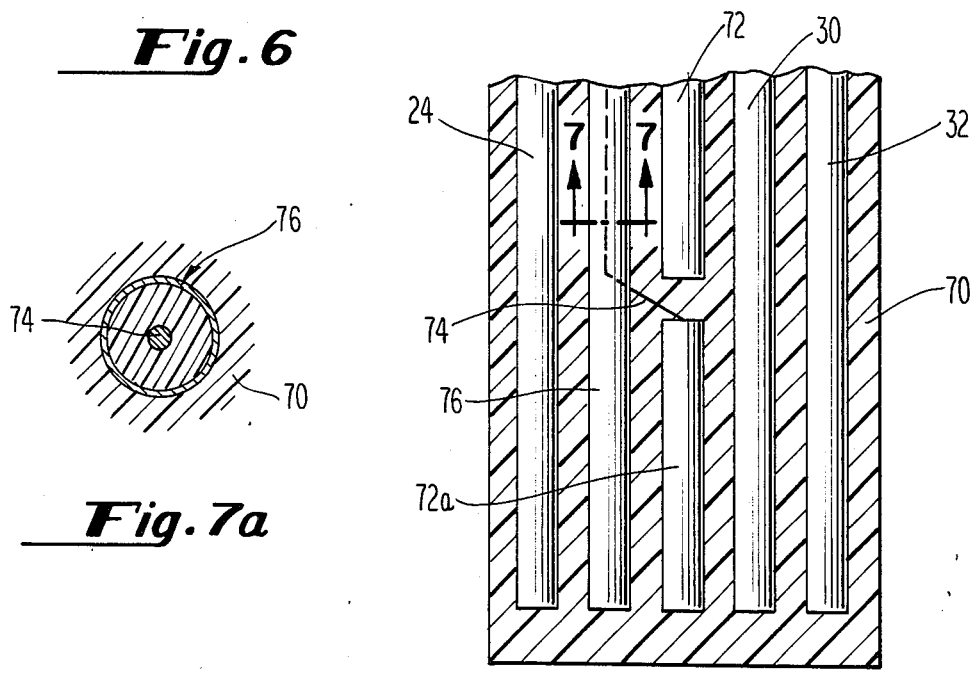
Fig. 7a
Fig. 7
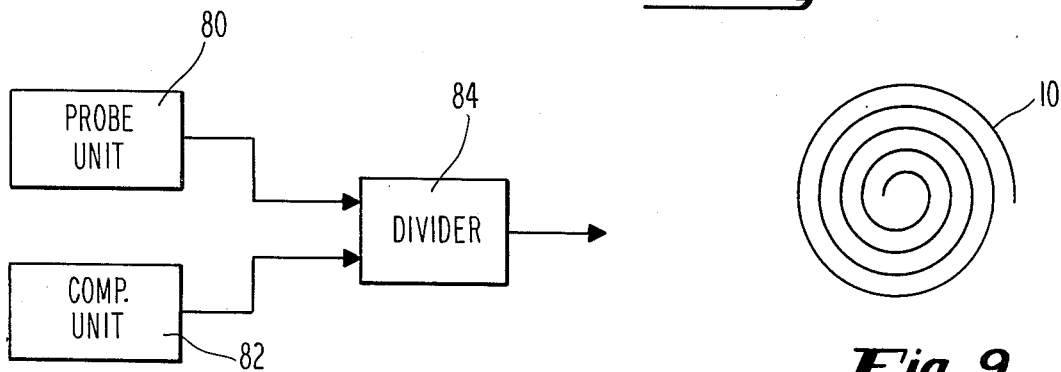
Fig. 8
Fig. 9

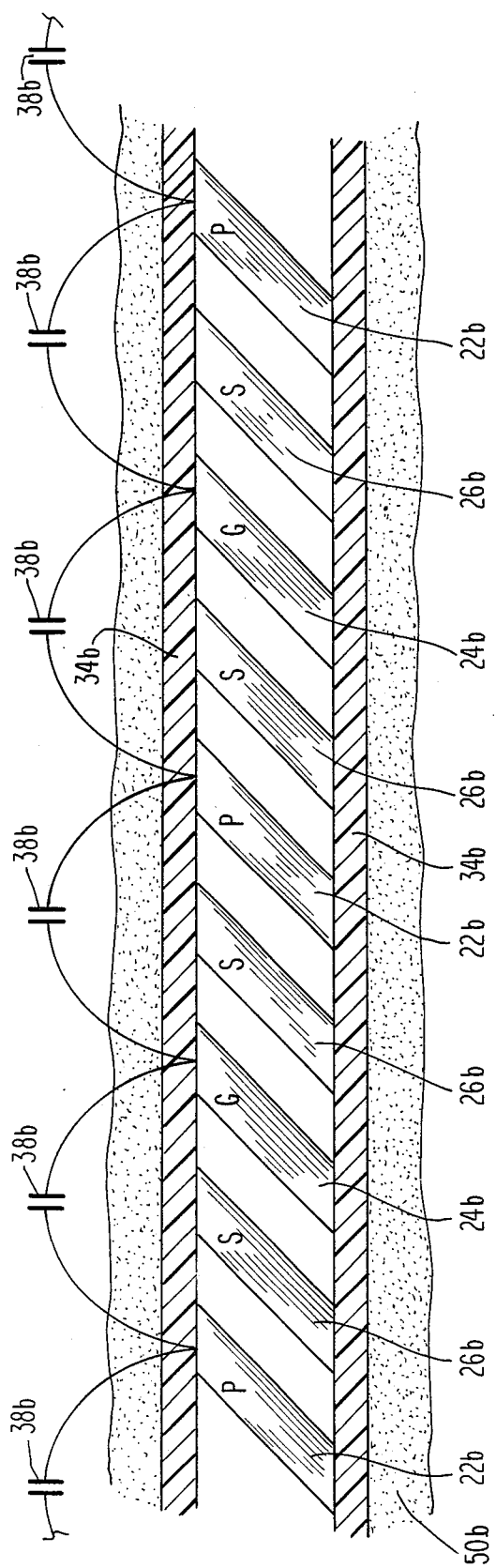
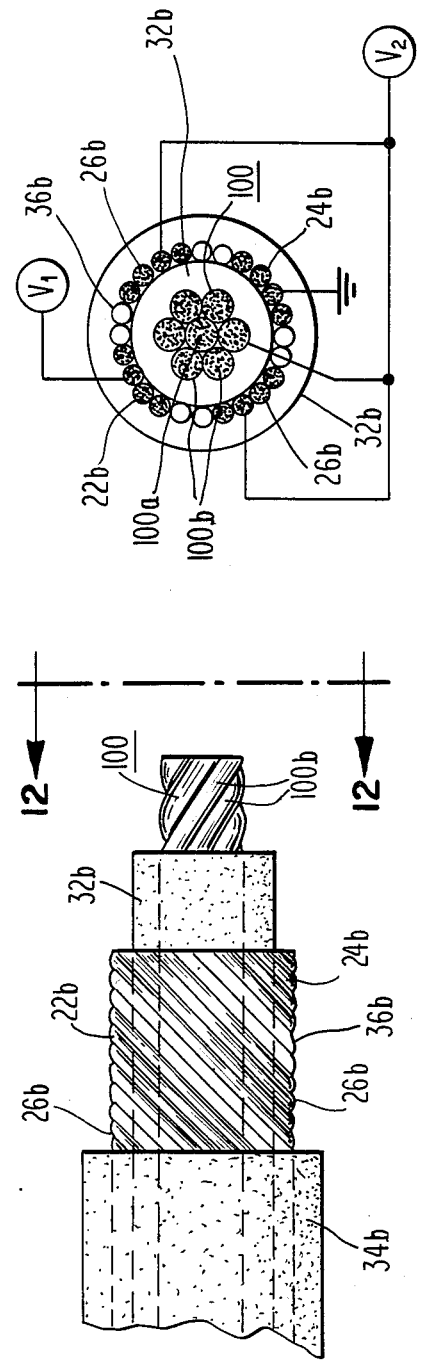
Fig. 10
Fig. 11
Fig. 12

PROBE SYSTEM FOR MEASURING THE CONDITION OF MATERIALS

BACKGROUND OF THE INVENTION

This invention relates to probes of the type which are adapted to be driven by an AC signal and extend into the materials whose condition is being measured. More specifically, this invention is directed to an apparatus adapted to be driven by a radio frequency signal so as to measure changes in capacitance or susceptance as a function of the condition of materials within a vessel.

Probes of the RF type are disclosed in U.S. Pat. Nos. 4,064,753 and 4,166,388 assigned to the assignee of this invention. The probes as disclosed therein are essentially flexible and include longitudinally extending probe and guard electrodes which are surrounded with insulation. These probes are best suited for use in conductive materials which provide a radio frequency ground in intimate contact with the measuring region of the probe insulation. Therefore, measurement of insulating materials do not conveniently lend themselves to the use of such probes. For example, some vessels have non-vertical walls which cause an undesirable nonlinearity of capacitance change per change in material level when using a probe which measures to the walls of the vessel. It may also be difficult to avoid movement of the probe with respect to the wall and this too can create inaccuracies in measuring the condition of materials. Furthermore, many vessels are not grounded, necessitating the installation of a ground or reference electrodes in a uniform geometrical relationship. For vessels which are suitable for using such a probe, it is not possible to reliably calibrate the probe until the probe is installed within the vessel since the exact geometrical relationship between the probe and the vessel is not known.

Another probe for measuring the levels of liquids within a vessel is disclosed in U.S. Pat. No. 3,918,306 which is assigned to the assignee of this invention. The probe includes exposed parallel probe and ground electrodes for measuring the level of fluid between the exposed electrodes. Such probes may not be used with conductive liquids. Moreover, the probe structure including the ground and probe electrodes is substantially rigid so as to make it difficult to insert an elongated probe vertically into a vessel having a minimal overhead clearance. Moreover, elongated probes (e.g., probes having a length of 20 feet or more) are not readily manufacturable and transportable. Furthermore, such probes which incorporate a guard electrode which is not coextensive with the ground and probe electrodes are adversely affected by coatings which collect on the probe above the level of the material whose condition is being measured. See also, U.S. Pat. No. 3,285,068 and U.S. Pat. No. 3,079,797 for a disclosure of rigid probe and ground electrodes where at least one of the electrodes is exposed to the fluid whose level is being measured.

U.S. Pat. No. 4,208,909 is also assigned to the assignee of this invention and discloses the use of a level measuring probe as well as a dielectric constant compensating probe. However, the probe does not include a guard electrode interposed between any probe electrode and ground electrode. Moreover, the probe is rigid posing more of the above-discussed problems.

SUMMARY OF THE INVENTION

It is an object of this invention to provide a method and apparatus for measuring the condition of materials which is independent of the nature of the vessel in which the materials are located, e.g., linear with level.

It is a further object of this invention to provide a method and apparatus for measuring the condition of materials in ungrounded vessels.

It is a further object of this invention to provide a method and apparatus for measuring the condition of material in vessels where there is minimal overhead clearance.

It is a further object of this invention to provide a method and apparatus for measuring the condition of materials which is independent of movement between the measuring mechanisms and the walls of the vessel in which the materials are contained.

It is a still further object of this invention to provide a method and apparatus for measuring the condition of materials which may be calibrated before installation.

It is a further object of this invention to provide a method and apparatus for measuring the condition of materials which is independent of any coating of material on the mechanisms utilized in measuring the condition.

It is a still further object of this invention to provide a method and apparatus for measuring the condition of materials which is independent of the dielectric constant of the materials and any variations in the dielectric constant of insulation associated with the mechanism for measuring the condition of materials.

It is a further object of this invention to provide a method and apparatus which is readily manufacturable and transportable.

It is a further object of this invention to provide a method and apparatus which is strong.

It is a further object of this invention to provide a method and apparatus which maximizes the surface area of the measuring electrodes per unit length of the probe.

It is a further object of this invention to provide a method and apparatus which is bendable.

It is a further object of this invention to provide a terminal assembly for a probe which permits adjustment of the probe position while at the same time clamping the probe so as to prevent the probe from being pushed out, for example, by high pressure within the vessel, or pulled into the vessel itself.

It is a further object of this invention to provide a method and apparatus which is reliable and inexpensive.

In accordance with these and other objects of the invention, the preferred embodiment of the invention comprises a probe system for measuring the condition of materials wherein the system includes an elongated probe. The probe comprises a conductive probe electrode extending longitudinally along the probe, a conductive ground electrode extending longitudinally along the probe and laterally displaced with respect to the probe electrode and a conductive guard electrode extending longitudinally along the probe and interposed between the probe electrode and the ground electrode. Solid insulation means surrounds and mutually insulates the probe electrode, the ground electrode as well as insulating these electrodes from the materials. Means are provided for maintaining the guard electrode at substantially the same potential as the probe electrode.

In several embodiments of the invention, a second guard electrode extends longitudinally along the probe and the probe electrode is interposed between the two guard electrodes with additional insulation means insulating the second guard electrode from the probe electrode and the materials and means are provided for maintaining the second guard electrode at substantially the same potential as the probe electrode. A second ground electrode also extends longitudinally along the probe such that the second guard electrode is interposed between the probe electrode and the second ground electrode with additional insulation means insulating the second ground electrode from the second guard electrode and the materials.

In one embodiment of the invention, the electrodes comprise metallic strips having substantially rectangular cross-sections. In another embodiment of the invention, the electrodes comprise metallic wires having a substantially circular cross-section.

In a particularly preferred embodiment of the invention, a probe electrode, the ground electrode and a guard electrode are helical in configuration and extend longitudinally along the probe. Preferably, a second guard electrode of the configuration is utilized where the probe electrode is interposed between the guard electrodes, longitudinally along the probe. Preferably, a third guard electrode is centrally located and extends longitudinally through the probe such that the probe electrode, the ground electrode and the other two guard electrodes surround the third centrally located guard electrode such that the probe electrode and the ground electrode are in mutually opposing positions and the other two guard electrodes are in mutually opposing positions.

In this particularly preferred embodiment of the invention, the probe electrode, the ground electrode and the other two guard electrodes comprise a plurality of conductors and the centrally located guard electrode comprises a plurality of strands having a greater tensile strength than the other electrodes.

In the particularly preferred embodiment of the invention, a probe termination assembly includes shield means encircling the elongated probe and extending longitudinally along the probe. Support means encircle the shield means and extends longitudinally along the probe. A first sealing means is located between the shield means and support means and a second sealing means is located between the shield means and the probe so as to permit the probe to slide through the shield means.

In the preferred embodiment of the termination assembly, a clamping means secures the centrally located guard electrode to the support means so as to prevent the probe from being blown out of the termination assembly or pulled through the termination assembly. Preferably, the clamping means comprises a drum socket which engages the centrally located guard electrode.

In the various embodiments of the invention, the solid insulation means comprises a polymer of tetrafluoroethylene, a high density polyethylene or other suitable material.

In another embodiment of the invention, a second probe electrode is provided which is longitudinally displaced from the first probe electrode and extends longitudinally along the probe. A conductor is connected to the second probe electrode and conductive shield means are interposed between the conductor and the first probe electrode. The conductive shield means is also interposed between the conductor and the ground electrode. For this purpose, at least one of the guard electrodes may comprise a substantially tubular portion through which the conductor passes.

In accordance with this invention, the driving of the probe electrode(s) and the guard electrode(s) at substantially the same potential prevents RF current flow through a coating of the material being measured which may adhere to the probe above the level of material in the vessel which would otherwise cause an erroneous level indication.

BRIEF DESCRIPTION OF THE DRAWINGS

FIG. 6 is a schematic diagram of circuitry for measuring the capacitance of the materials in which the probe of this invention is immersed or surrounded;

FIG. 7 is a sectional view of a probe representing another embodiment of the invention;

FIG. 7a is a sectional view of the probe shown in FIG. 7 taken along line 7—7;

FIG. 8 is a block diagram of a circuit utilized with a robe of FIG. 7 and FIG. 7a;

FIG. 9 is a diagram of a probe constructed in accordance with this invention in coiled form;

FIG. 10 is a schematic diagram of a particularly preferred embodiment of the invention;

FIG. 11 is a broken away view of the particularly preferred embodiment of the invention;

FIG. 12 is a sectional view of the particularly preferred embodiment of the invention;

DETAILED DESCRIPTION OF A PREFERRED EMBODIMENT

Figure 1:
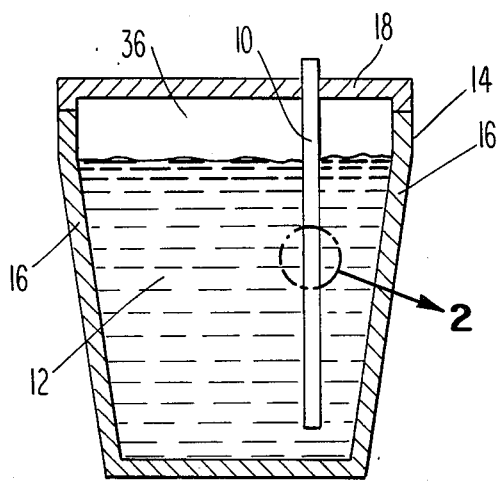
FIG. 1 is a sectional view of a vessel incorporating a probe constructed in accordance with this invention.

Referring to FIG. 1, a probe 10 for measuring the condition or level of materials 12 in a vessel 14 is shown. It will be noted that the vessel 14 comprises upwardly and outwardly extending walls 16 which vary in distance from the probe 10. It will also be noted that the vessel 14 is ungrounded and comprises a non-conductive material. Furthermore, the vessel 14 is covered by a lid 18 which is permanently attached to the walls 16. An overhead ceiling limits the space above the lid 18.

The non-parallel or otherwise irregular relationship between the probe 10 and the walls 16, the ungrounded non-conductive nature of the vessel 14 and the limited overhead room between the lid 18 and any overhead obstruction, such as a ceiling, have created problems in the prior art. The probe constructed in accordance with this invention eliminates such problems as will now be discussed in greater detail with reference to FIGS. 2 and 3.

Figure 2:
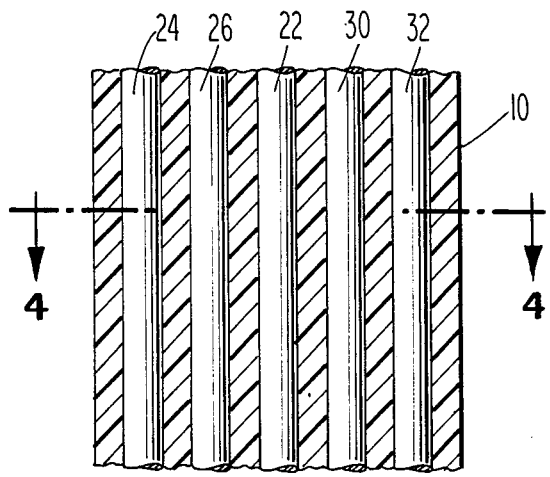
FIG. 2 is a sectional view of the probe shown in FIG. 1.
Figure 3:
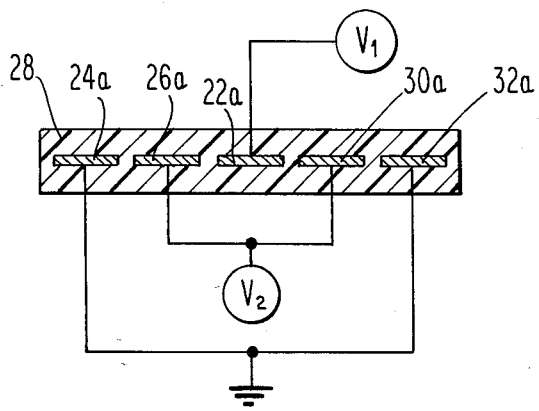
FIG. 3 is a sectional view of another probe.
Figure 4:
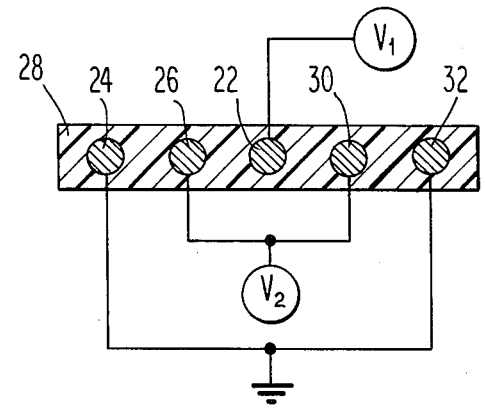
FIG. 4 is a sectional view of the probe shown in FIG. 2 taken along line 4—4.

As shown in FIGS. 2 and 4, the probe 10 includes a conductive probe electrode 22 extending longitudinally along the probe and a longitudinally extending ground electrode 24 which also extends along the probe but is laterally displaced from the probe electrode 22. A conductive guard electrode 26 extends longitudinally along the probe and is interposed between the probe electrode and the ground electrode in substantial alignment as best shown in FIG. 3. Solid insulation means 28 such as a polymer of tetrafluoroethylene surrounds and mutually insulates the probe electrode 22, the ground electrode 24 and the guard electrode 26.

In accordance with one important aspect of the invention, the probe electrode 22 and the guard electrode 26 are driven by voltages V1 and V2 which are substantially equal. The ground electrode 24 is, of course, grounded. As will be explained in greater detail with reference to FIG. 5a and disclosed in U.S. Pat. Nos. 4,064,753 and 4,166,388, incorporated herein by reference, this drive of the probe electrode 22 and guard electrode 26 allows the probe 10 to ignore coatings on the probe which might otherwise lead to an erroneous measurement of the condition or level of materials 12 as shown in FIG. 1. A second longitudinally extending guard electrode 30, as well as a second longitudinally extending ground electrode 32, are also incorporated in probe 10. As shown in FIG. 4, all of the electrodes 22, 24, 26, 30 and 32 are substantially aligned.

As shown in FIG. 3, the electrodes 22a, 24a, 26a, 30a and 32a comprise substantially planar metallic strips having substantially rectangular cross-sections. This is in contrast to the substantially circular configurations as shown in FIG. 4 in which a probe electrode 22, ground electrodes 24 and 32 and guard electrodes 26 and 30 comprise metallic wires.

Figure 5A:
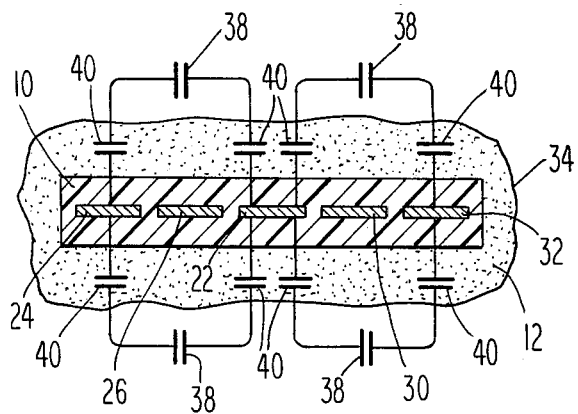
FIG. 5a is an equivalent circuit of the probe shown in FIG. 3 with a coating of materials accumulated on the probe.
Figure 5B:
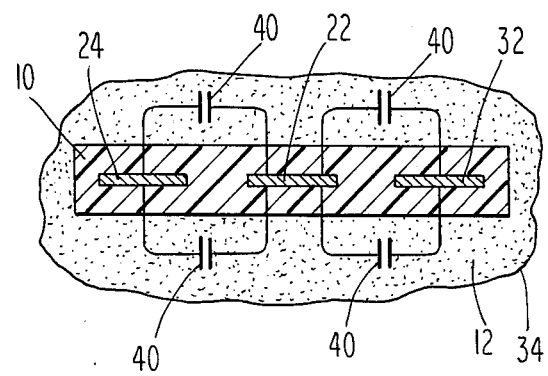
FIG. 5b represents the equivalent circuit of the probe of FIG. 5a with the guard electrodes eliminated.

Referring now to FIG. 5a, the probe 10 as depicted is carrying a substantial coating 34 of adhering materials 12. Despite this coating 34, the probe 10 is able to function properly, i.e., ignore the coating 12, for the following reasons. As shown in FIG. 5a, an equivalent circuit of the probe in the vicinity 36 above the materials 12 shown in FIG. 1 is represented by the air capacitance 38 between the probe electrodes 24 and 32. This air capacitor or susceptance 38 is in series with capacitances or susceptances 40 of the coating 34 itself. Since the capacitance 38 is small relative to the series capacitance 40, the capacitance 38 is readily distinguishable from the capacitance through the materials 12 below the uppermost level of the materials so as to provide an appropriate indication of the material level. However, if the guard electrodes 26 and 30 were eliminated as shown in FIG. 5b, the equivalent circuit of FIG. 5a would be converted to the equivalent circuit of FIG. 5b wherein the only capacitance between the probe electrode 22 and the ground electrodes 24 and 32 would be represented by the capacitances 40 through the coating 34. Such capacitances would, of course, be indistinguishable from the capacitance through the materials 12 themselves so as to provide no indication of level or other condition of the materials 12.

Referring now to FIG. 6, a circuit is shown for driving the probe 10. The circuit includes a fixed frequency oscillator 50 which is coupled to a transformer 54 including a primary 52, and a secondary 56 forming part of a bridge network including a capacitor 58 and a capacitance 60 which represents the overall capacitance of the probe 10 from the probe electrode 22 to the ground electrodes 24 and 32. The guard electrodes 26 and 38 are connected to a tap 61 on the secondary 56 which is also connected to an input terminal on amplifier 62. The probe electrode 22 is connected to the junction of capacitors 58, 60 and 64, and is also connected to the second input terminal of amplifier 62. The guard electrodes 26 and 30 are driven at substantially the same potential as the probe electrode 22 because the large value of capacitor 64 relative to capacitors 58 and 60 provides a low impedance between the probe and guard terminals. The signal at an output terminal 66 of the amplifier 62 is indicative of the capacitance or susceptance of the materials and hence the condition or level of the materials 12 within the vessel 14. In the circuit shown in FIG. 5a, the guard electrodes 26 and 30 will always be driven at substantially the same potential as the probe electrode 22. An additional method of driving the probe electrode 22 at the same voltage as the guard electrodes 26 and 30 is to connect the probe electrode 22 to the input of a unity-gain voltage amplifier. The low impedance output of the amplifier is connected to the guard electrodes 26 and 30. An appropriate circuit for these purposes is disclosed in U.S. Pat. No. 4,166,388 at FIG. 23 which is incorporated herein by reference.

In some instances, it may be desirable to compensate for variations in the dielectric constant of the materials 12 within the vessel 14, as well as variations in the dielectric constant of the probe insulation 28 where such variations may occur as a function of the particular material being measured or temperature. A probe 70 suitable for such purposes is disclosed in FIG. 7. This probe 70 includes longitudinally extending ground electrodes 24 and 32 and a longitudinally extending guard electrode 30. However, the probe electrode 72 is separated from a longitudinally extending compensation electrode 72a. The compensating electrode 72a is coupled to a conductor 74 which extends into and through a cylindrical guard electrode 76 as best shown in FIG. 7a. The compensating electrode 72a functions in a manner similar to the compensating probe electrodes disclosed in U.S. Pat. No. 4,208,909 which is incorporated herein by reference. In this connection, reference is made to FIG. 8 wherein the probe unit electronics 80 coupled to the probe electrode 72 and compensating unit electronics 82 coupled to the compensating electrode 72a are supplied to a divider network 84 and generate an output which is independent of variations of the dielectric constant of the materials 12 and/or the dielectric constant of the insulation.

In accordance with this invention, the probe 10 as well as the probe 70 is bendable and may be coiled as shown in FIG. 9. This, of course, is an important factor in allowing the probe to be utilized in a space having a minimal overhead. It will also be appreciated that such a probe is simple, rugged, reliable and inexpensive and can be manufactured and transported in long lengths.

Reference will now be made to FIGS. 10–12, wherein the particularly preferred embodiment of the invention is shown. Referring first to FIGS. 11 and 12, an elongated probe comprises a probe electrode $22b(p)$, a ground electrode $24b(g)$ and a first and second guard electrode $26b(s)$. As shown in FIG. 11, the probe electrode, the ground electrode and the first and second guard electrodes are helical in configuration so as to extend longitudinally along the probe such that the probe electrode $22b$ is separated from the ground electrode by an interposed guard electrode in each position along the length of the probe.

As also shown in FIGS. 11 and 12, the probe comprises a third guard electrode 100, which comprises a plurality of strands (100b) of high tensile strength material such as steel, contrasted with copper or beryllium copper utilized in the probe electrode 22b, the ground electrode 24b, and the first and second guard electrodes 26b. The third guard electrode 100 is separated from the other electrodes by an insulating material 32b, such as high density polyethylene. A similar material may be utilized as an insulating jacket 34b.

As shown in FIGS. 11 and 12, the helical electrodes 22b, 24b and 26b comprise a plurality of strands, i.e., four have been shown. There are also strands of helical insulation 36b which separate the helical electrodes. The strands of helical insulation 36b may comprise high density polyethylene as well.

The probe shown in FIGS. 11 and 12 is particularly advantageous since it provides a substantial length of electrode per unit length of probe due to the helical configuration. Moreover, the centrally located guard electrode 30b provides substantial strength to the probe. Yet, the probe remains flexible or bendable.

Referring now to FIG. 10, a schematic representation is presented which illustrates the effectiveness of the guard electrode. For clarity, the helical probe electrode 22b has been identified with the letter 'p', the helical guard electrode 26b has been identified with the letter 's', and the helical ground electrode 24b has been identified with the letter 'g'. Due to the presence of the guard electrodes 26b, the probe to ground capacitance 38b extends outwardly through the air even in the presence of a coating 50b, due to the presence of the guard electrodes 26b. By driving the guard electrode 26b at substantially the same potential as the probe electrode 22b, any probe to ground capacitance through the insulation or coating only is substantially eliminated. It will, of course, be appreciated that capacitance or susceptance 38b is in series with a much larger capacitance or susceptance through the coating 50b which has no significant effect on the measured capacitance or susceptance 38b.

The termination assembly for the probe shown in FIGS. 10-12 will now be described with reference to FIGS. 13-15. The termination assembly is adapted to be mounted and supported on a tank (not depicted) by means of a connector 102 having a threaded end 104 such that it may be screwed into an appropriately sized hole in the tank. A conductive shield 106 is connected to the potential of the guard electrode on up into a housing 108. The shield 106 which surrounds the probe with the helical electrode assures no leakage path to ground from the probe electrode.

In accordance with one important aspect of the invention, the exterior insulation 34b of the probe is in contact with an O-ring 110 which is contained within annular members 112 and 114 which are conductive and form part of the conductive shield 106. The O-ring 110 allows the probe including the insulating material 34b to slide relative to the conductive shield 106 while preventing escape of materials upwardly along the probe and surface of the insulation 34b. Additional sealing is provided along the exterior of the conductive shield 106 by means of annular sealing members 116 and 118 which contact an exterior cylinder of insulation 120 positioned radially outwardly from the conductive shield 106.

In accordance with another important aspect of the invention, despite the ability to slide the probe through the O-ring seal 110, the probe can be firmly clamped in place so as to preclude any possibility of the probe blowing out due to pressure within the vessel or the probe to be pulled into the vessel. This is accomplished oy means of securing the central guard electrode member 30b to a cap 122. The cap 122 includes an opening 124 receiving the central guard electrode member 30b which extends upwardly through a lower portion 126 which is secured to the cap 122. The upper portion 128 is threaded onto the lower portion and wedges the central guard electrode member 30b between the upper and lower portions so as to secure the central guard electrode member 30b in place.

Figure 15:
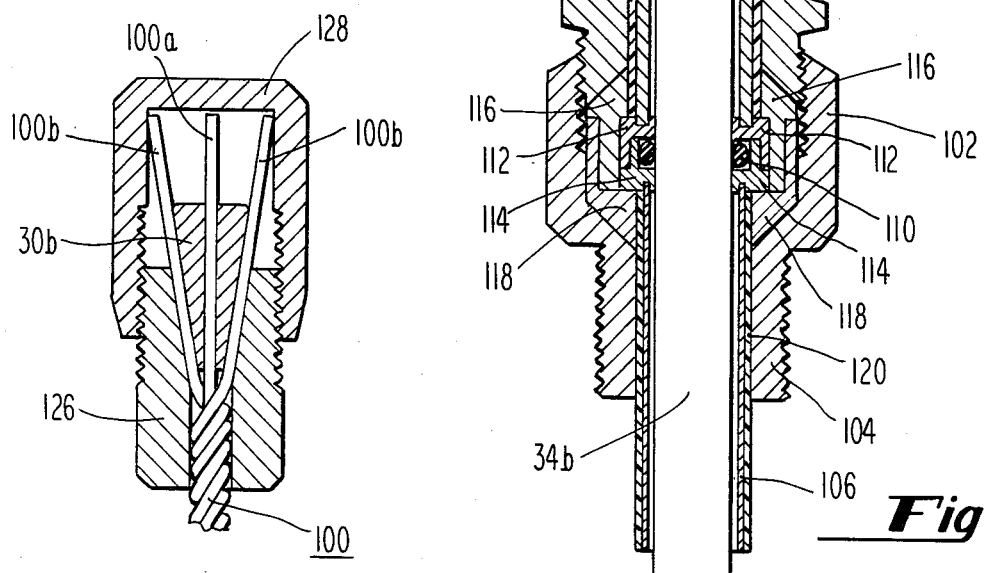
FIG. 15 is a sectional view taken along line 15—15 in FIG. 14.

As shown in FIG. 15, the individual outer braids 100b are separated from the central braid 110a of the supporting wire rope cable 100 and a holding member 30b having a central bore to receive the central braid 100a is wedged between the outer braids 100b and the inner tapered bore of the lower member 126, thereby securing the end of the cable 100. Cable termination assemblies of the type described are sold under the designation drum socket assembly by the Electroline Division of Union Metal Manufacturing Co., Canton, Ohio.

Figure 13:
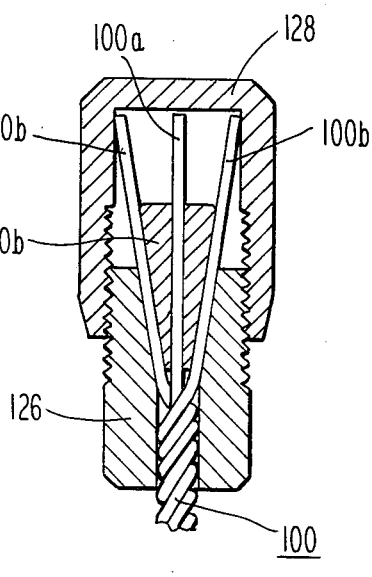
FIG. 13 is a sectional view of a termination assembly employed with the particularly preferred embodiment of the invention.
Figure 14:
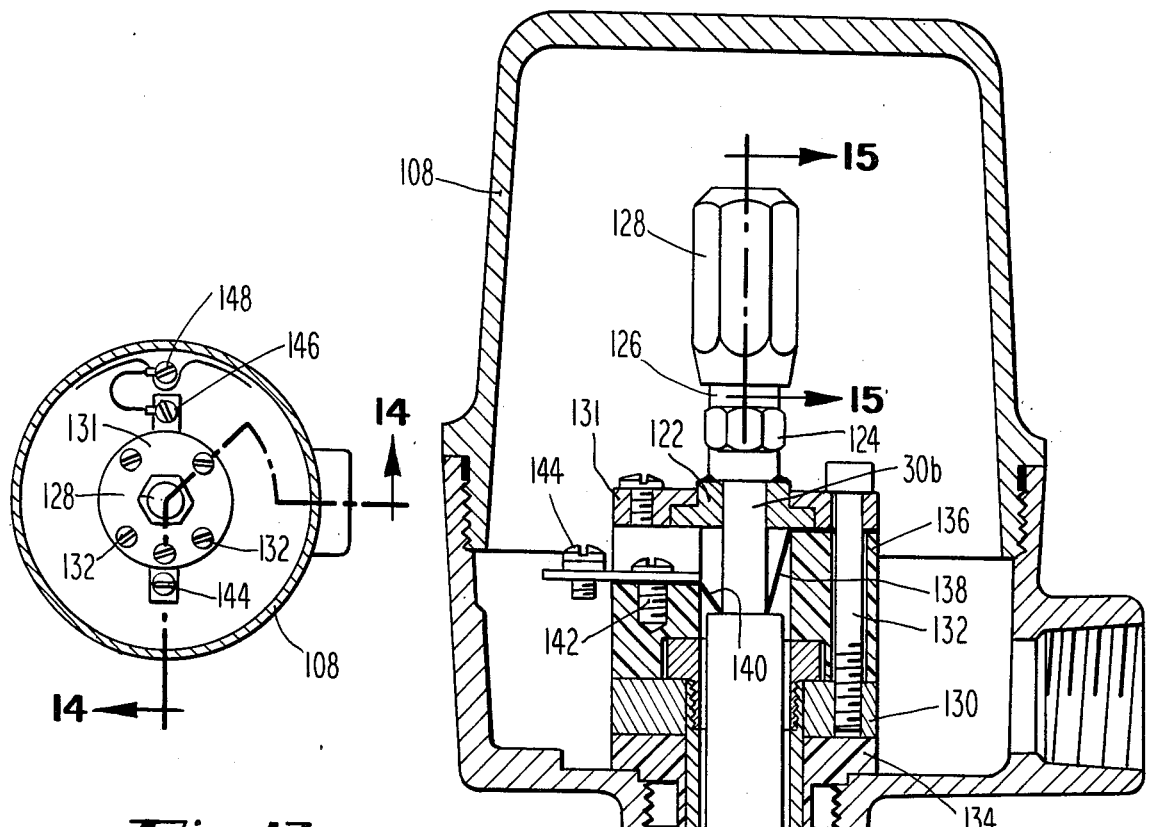
FIG. 14 is a sectional view of the termination assembly shown in FIG. 13 taken along line 14—14.

The cap 122 is secured to a lower ring 130 by means of a collar 131 and bolts 132 shown in FIGS. 13 and 14. The ring 130 is secured to the upper portion of the conductive shield 106. Insulation 134 separates the ring 130 from the housing 108.

It will be appreciated that the cap 122 and the ring 130 are maintained at the same potential as the shield 106 which is the same potential as the guard electrode. This is accomplished through a connection 138. A connection 140 is made to terminal posts 142 and 144 which are at the probe electrode potential. Terminals 146 and 148 are connected to the ground electrode and ground potential.

It will be appreciated that a terminal assembly as shown in FIGS. 13-15 may be utilized with other probes where sealing and engaging is maintained between the probe itself and a sealing ring while one or more of the electrodes is clamped in place so as to prevent movement of the probe. At the same time, the probe may be shortened by simply unclamping and sliding the probe along the sealing ring.

Although a particular material for the insulation 28 has been described, it will be appreciated that other insulation materials may be utilized. In addition, other modifications in the various embodiments disclosed will occur to those of ordinary skill in the art. It will therefore be understood that these various modifications and other embodiments will fall within the true spirit and scope of the invention as set forth in the appended claims.

We claim:

1. A probe system comprising:
   an elongated probe including at least one electrode; and
   a probe termination assembly including:
   shield means encircling said elongated probe, said shield means extending longitudinally along said probe;
   support means encircling said shield means, said support means extending longitudinally along said probe;
   first sealing means between said shield means and said support means;

second sealing means between said shield means and said probe, said second sealing means adapted to permit said probe to slide through said shield means; and a clamping means for securing said at least one electrode to said support means.

2. A probe system for measuring the condition of materials in a vessel, the probe system comprising:
an elongated probe including:
a conductive probe electrode extending longitudinally along said probe,
a conductive ground electrode extending longitudinally along said probe and laterally displaced from said probe electrode,
a first conductive guard electrode extending longitudinally along said probe and interposed between said probe electrode and said ground electrode,
solid insulation means surrounding and mutually insulating said probe electrode, said first conductive guard electrode, said ground electrode and said material;
means for maintaining the potnetial of said first guard electrode at substantially the potential of said probe electrode; and
a second guard electrode extending longitudinally along said probe, said probe electrode being interposed between said first guard electrode and said second guard electrode, aid solid insulation means insulating said second guard electrode from said probe electrode and said material, said means for maintaining the potential of said first guard electrode also maintaining the potential of said second guard electrode at substantially the potential of said probe electrode.

3. The probe system according to claim 2 further comprising a second ground electrode extending longitudinally along said probe, said second guard electrode being interposed between said probe electrode and said second ground electrode, said additional insulation means insulating said second guard electrode from said second guard electrode and said materials.

4. The probe system of claim 2 wherein said electrodes are metallic strips having substantially rectangular cross-sections.

5. The probe system according to claim 2 wherein said electrodes comprise a plurality of metallic wires having substantially circular cross-section.

6. The probe system according to claim 2 wherein said solid insulation comprises a polymer of tetrafluoroethylene.

7. A probe system for measuring the condition of materials in a vessel, the probe system comprising:
an elongated probe including:
a conductive probe electrode extending longitudinally along said probe,
a conductive ground electrode extending longitudinally along said probe and laterally displaced from said probe electrode,
a first conductive guard electrode extending longitudinal along said probe and interposed between said probe electrode and said ground electrode,
a solid insulation means surrounding and mutually insulating said probe electrode, said first conductive guard electrode, said ground electrode and said material;
means for maintaining the potnetial of said first guard electrode at substantially the potnetial of said probe electrode;
a second probe electrode extending longitudinally along said probe and longitudinally displaced from said probe electrode;
a conductor connected to said second probe electrode; and
a cylindrical guard electrode interposed between said conductor and said probe electrode and between said conductor and said ground electrode.

8. A probe system for measuring the condition of materials in a vessel, the probe system comprising:
an elongated probe including;
a conductive probe electrode extending longitudinally along said probe;
a conductive ground electrode extending longitudinally along said probe and laterally displaced from said probe electrode;
a first conductive guard electrode extending longitudinally along said probe and interposed between said probe electrode and said ground electrode;
a second guard electrode extending longitudinally along said probe, said probe electrode being interposed between said first guard electrode and said second guard electrode;
solid insulation means surrounding and mutually insulating probe electrode, said first guard electrode, said ground electrode and said material, said solid insulation means insulating said second guard electrode from said probe electrode and said material;
means for maintaining the potential of said first guard electrode at substantially the potential of said probe electrode, said means for maintaining the potential of said first guard electrode also maintaining the potential of said second guard electrode at substantially the potential of said probe electrode;
a third guard electrode centrally and longitudinally extending through said probe, said probe electrode, said ground electrode, said first guard electrode and said second guard electrode surrounding said third guard electrode, said probe electrode and said first guard electrode being in mutually opposing positions and said first guard electrodes and said second guard electrode being in mutually opposing positions;
wherein said probe electrode, said ground electrode, said first guard electrode, and said second guard eletrode are helical in configuration and extend longitudinally along said probe.

9. The probe system of claim 2 wherein said probe electrode, said ground electrode and said first guard electrode are helical in configuration extending longitudinally along said probe.

10. The probe system of claim 9 further comprising a second guard electrode helical in configuration extending longitudinally along said probe.

11. The probe system of claim 10 wherein said probe electrode is interposed between said first guard electrode and said second guard electrode extending longitudinally along said probe.

12. The probe system of claim 1 wherein said at least one electrode comprises a central guard electrode member and a plurality of helical electrodes surrounding said central guard electrode member.

13. The probe system of claim 8 wherein each of said probe electrode, said ground electrode, said first guard electrode and said second guard electrode comprises a plurality of conductors.

14. The probe system of claim 13 wherein said third guard electrode comprises a plurality of strands.

15. The probe system of claim 14 wherein said third first guard electrode has a greater tensile strength than said guard electrode and said second guard electrode.

16. The probe system of claim 13 further comprising a termination assembly including:
 support means;
 shield means encircling said elongated probe, said shield means extending longitudinally through said support means along said probe;
 first sealing means between said shield means and said support means; and
 second sealing means between said shield means and said probe, said second sealing means adapted to permit said probe to slide through said shield means.

17. The probe system of claim 16 comprising clamping means for securing said third guard electrode to said support means.

18. The probe system of claim 17 wherein said clamping means comprises a drum socket.

19. The probe system of claim 11 further comprising:
 a second probe electrode of helical configuration extending longitudinally along said probe and longitudinally displaced from said probe electrode;
 a conductor connected to said second probe electrode; and conductive shield means interposed between said conductor and said probe electrode and between said conductor and said ground electrode and said second guard electrode.

20. The probe system of claim 2 wherein said probe is bendable.

21. The probe system of claim 2 wherein said probe is adapted to be coiled.

22. The probe system of claim 12 further comprising means for maintaining the potential of said central guard electrode member and at leat two of said helical electrodes at subtantially the same potential.

* * * * *